United States Patent [19]

Inman et al.

[11] Patent Number: 4,951,666
[45] Date of Patent: Aug. 28, 1990

[54] THERMAL PACK

[75] Inventors: Joel D. Inman; Gary W. Pedersen; Timothy J. McKibben, all of Arlington, Tex.

[73] Assignee: Anago, Inc., Fort Worth, Tex.

[21] Appl. No.: 258,812

[22] Filed: Oct. 17, 1988

[51] Int. Cl.$^5$ .............................................. A61F 7/10
[52] U.S. Cl. .................................. 128/402; 383/901; 383/111; 383/63
[58] Field of Search .................... 383/36, 84, 98, 901, 383/102, 110, 111, 113; 128/402, 403, 379, 380; 62/530; 24/30.5 R

[56] References Cited

U.S. PATENT DOCUMENTS

| | | | |
|---|---|---|---|
| 785,638 | 3/1905 | Scritchfield | 383/111 |
| 858,550 | 7/1907 | Whall | 383/901 |
| 907,878 | 12/1908 | Pirtchard | 383/111 |
| 1,169,123 | 1/1916 | Burns | 128/402 |
| 1,576,488 | 3/1926 | Hodgson | 128/403 |
| 1,819,913 | 8/1931 | Miller | 383/901 |
| 2,072,564 | 3/1937 | May | 383/901 |
| 2,273,128 | 2/1942 | Madsen | 128/403 |
| 2,435,743 | 2/1948 | Geimer | 383/113 |
| 4,222,422 | 9/1980 | Lofberg | 383/111 |
| 4,372,318 | 2/1983 | Viesturs | 128/402 |
| 4,523,353 | 6/1985 | Hubbard et al. | 24/30.5 R |
| 4,530,220 | 7/1985 | Nambu et al. | 62/530 |
| 4,688,572 | 8/1987 | Hubbard et al. | 128/402 |

Primary Examiner—William H. Grieb
Assistant Examiner—Mark S. Graham
Attorney, Agent, or Firm—Charles D. Gunter, Jr.

[57] ABSTRACT

A Thermal Pack is shown for use in treating a localized injury. The pack includes a porous outer bag and a non-porous inner bag which is foldable between a retracted position within the outer bag and an extended position in which the inner bag protrudes from the outer bag for filling. A flap extends from the open mouth of the inner bag for creating a funnel to facilitate filling the inner bag when the inner bag is in the extended position.

6 Claims, 2 Drawing Sheets

THERMAL PACK

BACKGROUND OF THE INVENTION

1. Field of the Invention:

The present invention relates generally to therapeutic devices for the treatment of localized injury or pain and specifically to a device wrapable about a limb for the treatment of or prevention of injury thereto.

2. Description of the Prior Art:

It is well known that for therapeutic effect, muscle tissue should be heated in some circumstances and chilled in others. For instance, sprained or strained muscle tissues should be chilled to reduce swelling and further damage. Ice packs of various forms are known in the medical art and are commonly applied to localized injuries such as sprained or otherwise injured limbs. Small, specialized ice packs are known which are designed for application of cold to localized areas. The prior art ice packs typically include a pouch for holding ice and a strap or pair of straps for holding the pouch in contact with the localized area to be treated. The small, specialized ice packs, because of their size, typically have small pouch openings which are difficult to fill from an automatic ice machine or from a scoop from an ice bin. As a result, ice is often spilled as the pouch is filled and damage often occurs to the ice pack itself.

A need exists for a small, specialized ice pack which can be easily filled and refilled from an automatic ice machine or scoop from an ice bin.

A need also exists for such an improved ice pack which is simple in design and economical to manufacture.

SUMMARY OF THE INVENTION

The Thermal Pack of the invention includes a porous outer bag having an exterior, and interior and an open top. A non-porous inner bag is received within the outer bag and has an exterior, an interior and a mouth opening. The inner bag is foldable between a retracted position and an extended position in which the inner bag protrudes from the open top of the outer bag for filling. Seal means secure the mouth opening of the inner bag. A flap is located above the seal means for creating a funnel to facilitate filling the inner bag. A cuff is provided on the exterior of the inner bag to receive the fingers of a user's hand as the inner bag is being filled. Fastening means are provided for securing the open top of the outer bag when the inner bag is sealed and folded to the retracted position.

Additional objects, features and advantages will be apparent in the written description which follows.

DESCRIPTION OF THE PREFERRED EMBODIMENT

Figures 1, 2:
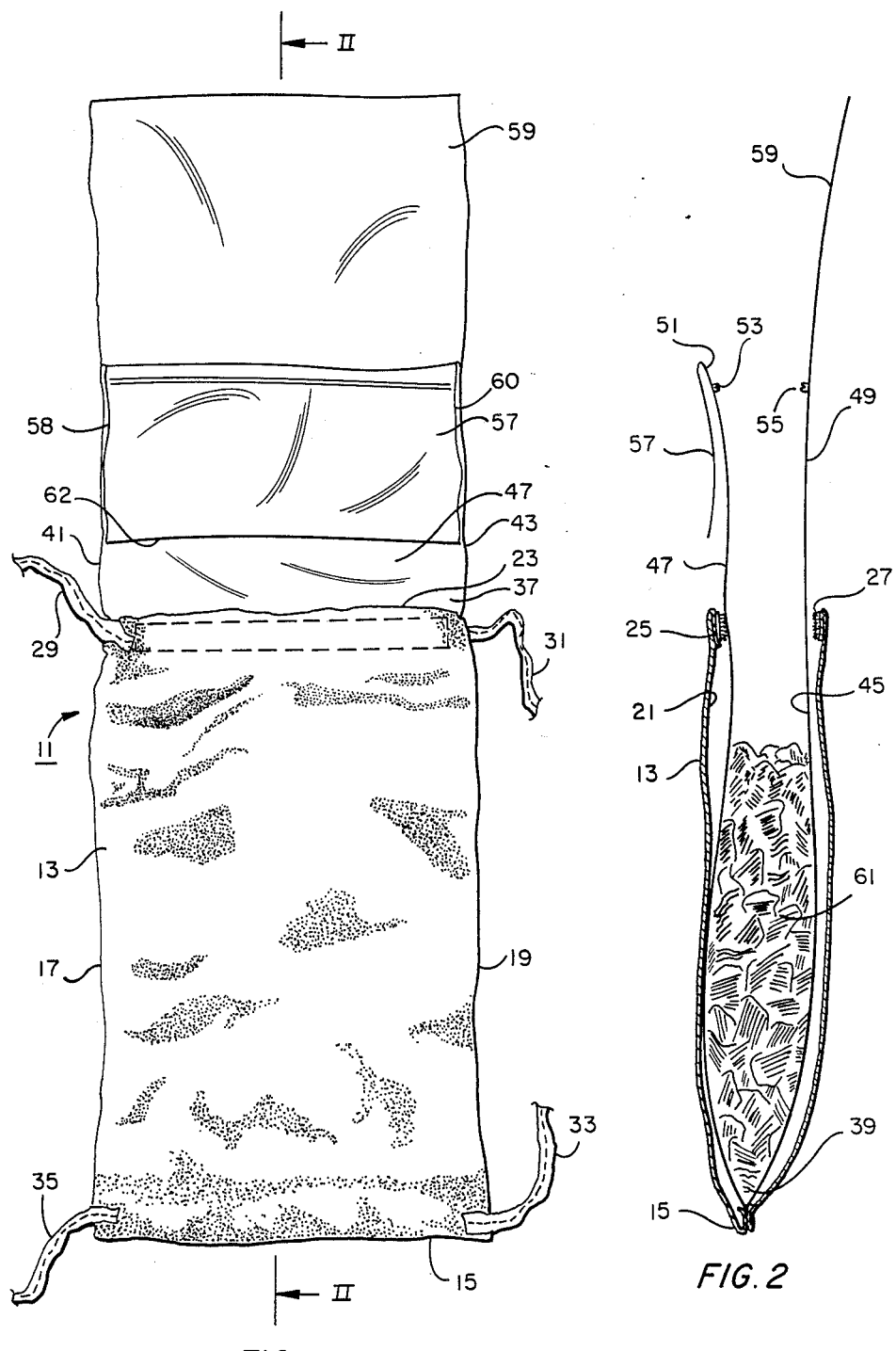
FIG. 1 is a prospective view of the ice pack of the invention showing the inner bag in the extended position with the flap protruding from the open top of the outer bag.
FIG. 2 is a side, cross-sectional view of the bag of FIG. 1 with the inner bag in the extended position.

FIG. 1 shows a thermal pack of the invention designated generally as 11. The pack 11 includes a porous outer bag 13 which is joined along the periphery on three sides thereof to form a bottom edge of 15 and opposing side edges 17, 19 which together define a bag interior 21 and an open top 23.

Figure 4:
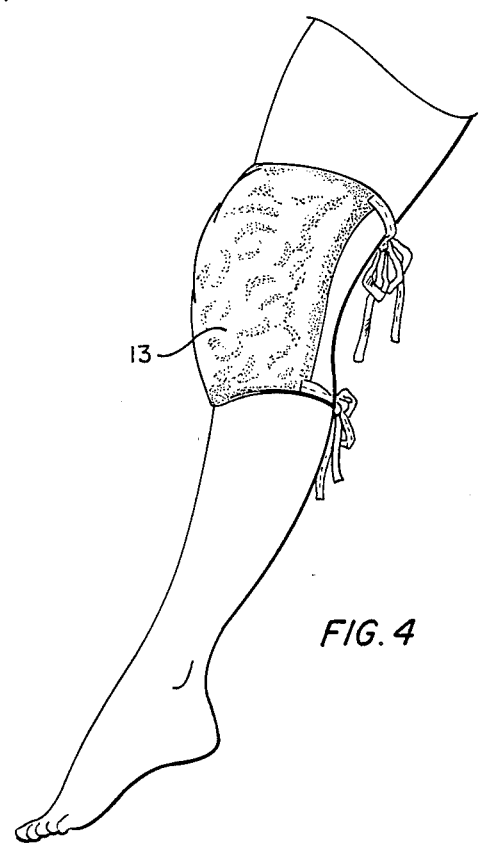
FIG. 4 is a side, elevational view of the ice pack of the invention wrapped about the knee joint of a wearer.

The outer bag 13 is preferably formed of a porous fabric such as a knitted, woven or stitched cloth material. Synthetic weaves such as polyester, nylon and rayon can also be utilized. As shown in FIG. 2, the outer bag 13 has fastening means such as Velcro strips 25, 27 for securing the open top 23. As is well known, one of the strips 25, 27 contains a plurality of hook-like elements while the other strip contains a brushed pile or loop type material. The strips 25, 27 are arranged transverse to the opposing side edges 17, 19 of the outer bag and are located within the interior 21 adjacent the open top 23. The outer bag 13 is also provided with a plurality of fastening straps 29, 31, 33, and 35 sewn to the respective bag corners. As shown in FIG. 4, the fastening straps allow the thermal pack 11 to be conveniently applied to a body part such as a person's limb.

Figure 3:
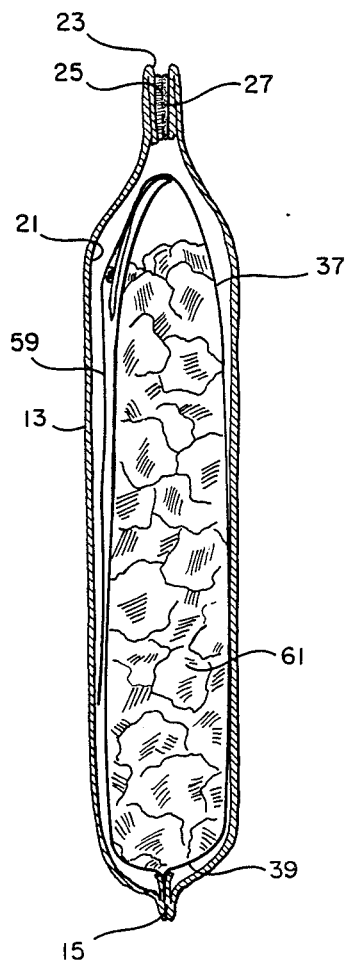
FIG. 3 is a side, cross-sectional view of the bag of FIG. 1 with the inner bag in the retracted position and the top of the outer bag being fastened.

As shown is FIGS. 1 and 2, the thermal pack 13 also includes a non-porous inner bag 37. Preferably, the non-porous bag 37 is constructed of a synthetic "plastic" material such as a water proof polyethylene or other inexpensive water proof material. The inner bag 37 also has a bottom edge 39 which is fastened along the bottom edge 15 of the outer bag within the interior thereof. The inner bag also has opposing side edges 41, 43 which define an interior 45, a planar top portion 47, a planar bottom portion 49, and a mouth opening 51. As shown in FIGS. 2 and 3, the inner bag 37 is foldable between an extended position (FIG. 2) in which the inner bag protrudes from the open top 23 of the outer bag 13 for filling and a retracted position (FIG. 3) wholly contained within the outer bag 13.

Seal means such as the sealing strips 53, 55 extend transversely to the side edges 41, 43 of the inner bag 37 for securing the mouth opening 51 of the inner bag. Preferably, the sealing strips 53, 55 comprise a pair of longitudinal sealing strips extending transversely to the side edges 41, 43 of the inner bag 13 for securing the mouth opening 51 of the inner bag. One of the sealing strips 53, 55 is provided with a protruding rib and the other of these sealing strips is provided with a mating groove for receiving the rib in press-fit fashion to form a water tight seal.

A longitudinal extension 59 is located above the sealing strip 55 and extends from the planar bottom portion 49 of the inner bag 37. The longitudinal extension 59 forms a flap for creating a funnel to 7 facilitate filling the inner bag 37 with ice or other particulate thermal media. For instance, an alternate thermal media is shown in U.S. Pat. No. 4,530,220, to Nambu et al, entitled "Deformable Bag for Use As Cooling Medium" which discloses a cooling medium which comprises a particulate gel prepared by casting an aqueous solution or suspension containing polyvinyl alcohol and a water soluble organic compound in a mold. It is also possible that heating media could be placed within the inner bag 37 such as hot liquid or particulate media.

The top planar portion 47 also has a longitudinal extension 57 which forms a cuff on the exterior of the non-porous inner bag for receiving the fingers of a user's hand. The longitudinal extension 57 has opposing side edges 58, 60 and is folded back over the exterior surface of the inner bag to form the cuff. The opposing side edges 58, 60 form opposing seams which run along the opposing side edges of the plastic inner bag. The cuff edge 62 forms an opening for the fingers of the user's hand.

As shown in FIGS. 2 and 3, the inner bag 37 is moved from the extended position (FIG. 2) to the retracted position (FIG. 3) by closing the sealing strips 53, 55 and then folding the flap 59 over the planar portion 47 within the outer bag interior 21 so that the fastening means 25, 27 can be used to close the open top 23.

In use, the outer bag 13 is held in one hand in the position shown in FIGS. 1 and 2. By pursing the bag side edges and open top, a funnel-like opening can be formed with the flap 59. The funnel-like opening then facilitates filling the bag with ice 61. For instance, the ice scoop from the ice machine can be inserted within the mouth opening with the flap 59 preventing any spillage. The cuff formed by longitudinal extension 57 provides a convenient means to grasp the inner bag and form the funnel-like opening.

An invention has been provided with several advantages. The thermal pack is suitable for use with any particulate thermal media, preferably crushed ice. The thermal pack is wrapable about the limb or other localized area to be treated. The outer bag is of a soft, porous material which is comfortable to wear and which absorbs condensed moisture. The inner bag is of a nonporous material to contain the thermal media. The folding design and flap extension and cuff opening of the inner bag provide a convenient means for filling the bag with ice without spilling or damaging the inner bag. The pack is simple in design and economical to manufacture.

Although the invention has been shown in only one of its forms, it is not thus limited but is susceptible to various changes and modifications without departing from the spirit thereof.

I claim:

1. An ice pack wrapable about a limb, the ice pack comprising:
   a cloth outer bag having an exterior, an interior and an open top;
   a plastic inner bag received within the outer bag, the inner bag having an exterior formed by opposing planar portions, an interior and a mouth opening for receiving ice, the inner bag being foldable between a retracted position wholly contained within the interior of the outer bag and an extended position in which the inner bag protrudes from the open top of the outer bag for filling;
   seal means for securing the mouth opening of the inner bag;
   a flap located above the seal means on a selected one of the opposing planar portions of the plastic inner bag for creating a funnel to facilitate filling the inner bag with ice;
   fastening means for securing the open top of the outer bag when the inner bag is sealed and folded to the retracted position within the outer bag; and
   a cuff formed on the exterior of the other of the opposing planar portions of the plastic inner bag, opposite the flap for receiving the fingers of a user's hand.

2. An ice pack wrapable about a limb, the ice pack comprising:
   a cloth outer bag having a bottom edge and opposing side edges which define a bag interior and an open top;
   a plastic inner bag received within the outer bag, the inner bag having a bottom edge which is fastened along the bottom edge of the outer bag and opposing side edges which define an exterior, an interior, a planar top portion, a planar bottom portion and a mouth opening for receiving ice, the inner bag being foldable between a retracted position wholly contained within the interior of the outer bag and an extended position in which the inner bag protrudes from the open top of the outer bag for filling;
   seal means extending transversely to the side edges of the inner bag for securing the mouth opening of the inner bag;
   a longitudinal extension located above the seal means and extending from the planar bottom portion of the inner bag for creating a funnel to facilitate filling the inner bag with ice;
   fastening means for securing the open top of the outer bag when the inner bag is sealed and folded to the retracted position within the outer bag; and
   a cuff formed on the exterior of the planar top portion of the plastic inner bag for receiving the fingers of a user's hand.

3. The ice pack of claim 2, wherein the cuff formed on the exterior of the top planar portion of the plastic inner bag includes a longitudinal extension having opposing side edges which is folded back over the exterior thereof, the opposing side edges of the cuff forming opposing seams which run along the opposing side edges of the plastic inner bag.

4. The ice pack of claim 2, wherein the seal means comprises a pair of longitudinal sealing strips extending transversely to the side edges of the inner bag for securing the mouth opening of the inner bag, one of the sealing strips having a protruding rib and the other of the sealing strips having a mating groove for receiving the rib in press-fit fashion.

5. The ice pack of claim 2, wherein the fastening means comprises a pair of hook and loop fastening strips arranged transverse to the opposing side edges of the outer bag within the interior thereof adjacent the open top.

6. The ice pack of claim 2, wherein the outer bag has a plurality of fastening straps connected proximate the opposing edges thereof for holding the ice pack about the limb of a user.

* * * * *